(12) United States Patent
Zhang et al.

(10) Patent No.: US 12,128,047 B2
(45) Date of Patent: Oct. 29, 2024

(54) TLR7 AGONIST AND PHARMACEUTICAL COMBINATION THEREOF FOR TREATING LUNG CANCER

(71) Applicant: CHIA TAI TIANQING PHARMACEUTICAL GROUP CO., LTD., Jiangsu (CN)

(72) Inventors: Xiquan Zhang, Jiangsu (CN); Ling Yang, Jiangsu (CN); Ying Zhang, Jiangsu (CN); Mincheng Zhang, Jiangsu (CN); Wei Song, Jiangsu (CN); Hongjiang Xu, Jiangsu (CN)

(73) Assignee: CHIA TAI TIANQING PHARMACEUTICAL GROUP CO., LTD., Jiangsu (CN)

( * ) Notice: Subject to any disclaimer, the term of this patent is extended or adjusted under 35 U.S.C. 154(b) by 908 days.

(21) Appl. No.: 17/058,979

(22) PCT Filed: May 24, 2019

(86) PCT No.: PCT/CN2019/088360
§ 371 (c)(1),
(2) Date: Nov. 25, 2020

(87) PCT Pub. No.: WO2019/223788
PCT Pub. Date: Nov. 28, 2019

(65) Prior Publication Data
US 2021/0220362 A1    Jul. 22, 2021

(30) Foreign Application Priority Data

May 25, 2018 (CN) .......................... 201810560770.X

(51) Int. Cl.
*A61K 31/519* (2006.01)
*A61P 35/00* (2006.01)

(52) U.S. Cl.
CPC ............ *A61K 31/519* (2013.01); *A61P 35/00* (2018.01)

(58) Field of Classification Search
CPC . C07D 487/04; A61K 31/519; A61K 31/5377
See application file for complete search history.

(56) References Cited

U.S. PATENT DOCUMENTS

2017/0202828 A1* 7/2017 Zhang .................... A61P 35/00
2017/0273983 A1* 9/2017 Ding ..................... C07D 487/04

FOREIGN PATENT DOCUMENTS

| CN | 105367576 | 3/2016 |
|---|---|---|
| CN | 107043377 | 8/2017 |
| CN | 107043379 | 8/2017 |
| CN | 107043380 | 8/2017 |
| EP | 3190113 | 7/2017 |
| JP | 2017-524037 | 8/2017 |
| WO | WO 2011/031965 | 3/2011 |
| WO | WO 2016/023511 | 2/2016 |
| WO | WO 2016/023511 A1 * | 2/2016 |
| WO | WO 2016/107536 | 7/2016 |
| WO | WO 2017/076346 | 11/2017 |
| WO | WO 2019/223788 | 11/2019 |

OTHER PUBLICATIONS

PCT International Search Report and Written Opinion in International Appln. No. PCT/CN2019/08836, dated Aug. 20, 2019, 19 pages.
Wang et al., "The TLR7 agonist induces tumor regression both by promoting CD4+T cells proliferation and by reversing T regulatory cell-mediated suppression via dendritic cells," Oncotarget, Dec. 15, 2014, 6(3):1779-1789.
Han et al., "Anlotinib as a third-line therapy in patients with refractory advanced non-small-cell lung cancer: a multicentre, randomised phase II trial (ALTER0302)," British Journal of Cancer, Feb. 13, 2018, 118:654-661.
JP Office Action in Japanese Appln. No. 2020-565840, dated May 18, 2023, 15 pages (with English translation).
Cherfils-Vicini et al., "Triggering of TLR7 and TLR8 expressed by human lung cancer cells induces cell survival and chemoresistance," Journal of Clinical Investigation, Apr. 2010, 120(4):1285-1297.
International Preliminary Report on Patentability in International Appln. No. PCT/CN2019/088360, dated Dec. 1, 2020, 9 pages.
Supplementary European Search Report in European Appln No. 19807809.9, dated Feb. 23, 2022 3 pages.

(Continued)

*Primary Examiner* — Deepak R Rao
(74) *Attorney, Agent, or Firm* — Fish & Richardson P.C.

(57) ABSTRACT

The present application relates to a compound of formula I as a toll-Like receptor 7 (TLR7) agonist or a pharmaceutically acceptable salt thereof for treating lung cancer, a pharmaceutical combination of the TLR7 agonist and a tyrosine kinase inhibitor for treating lung cancer, and the use of the compound of formula I or the pharmaceutically acceptable salt thereof and the pharmaceutical combination for treating lung cancer.

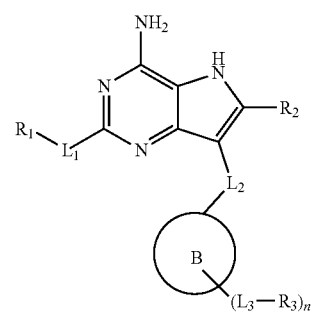

15 Claims, No Drawings

(56) References Cited

OTHER PUBLICATIONS

Chatterjee et al., "TLR7 Promotes Tumor Progression, Chemotherapy Resistance, and Poor Clinical Outcomes in Non-Small Cell Lung Cancer," American Association for Cancer Research, May 16, 2018, 74(18):1-11.

* cited by examiner

TLR7 AGONIST AND PHARMACEUTICAL COMBINATION THEREOF FOR TREATING LUNG CANCER

CROSS-REFERENCE TO RELATED APPLICATIONS

The present application claims the benefit and priority of the Chinese invention patent application No. 201810560770.X as filed with the China National Intellectual Property Administration on May 25, 2018, which is incorporated herein by reference in its entirety.

TECHNICAL FIELD

The present application relates to a toll like receptor 7 (TLR7) agonist and a pharmaceutical combination thereof. In particular, the present application relates to a TLR7 agonist for treating lung cancer, a use of a TLR7 agonist in the treatment of lung cancer, and a pharmaceutical combination of a TLR7 agonist and a tyrosine kinase inhibitor and a use of the pharmaceutical combination in the treatment of lung cancer.

BACKGROUND

Tyrosine kinases are a group of enzymes which catalyze the phosphorylation of tyrosine residues in proteins. They play an important role in intracellular signal transduction, take part in regulation, signaling and development of normal cells, and are closely related with proliferation, differentiation, migration and apoptosis of tumor cells. Many receptor tyrosine kinases are related with the formation of tumor, and can be classified as epidermal growth factor receptor (EGFR), platelet-derived growth factor receptor (PDGFR), vascular endothelial growth factor receptor (VEGFR), fibroblast growth factor receptor (FGFR) and the like according to the structure of an extracellular domain.

Toll like receptors are expressed in a variety of immune cells. Toll like receptors recognize highly conserved structural motifs: pathogen-associated molecular patterns (PAMPs) expressed by microbial pathogens or damage-associated molecular patterns (DAMPs) released by necrotic cells. Toll like receptors are stimulated by corresponding PAMPs or DAMPs to induce signaling cascade, resulting in activation of a transcription factor such as AP-1, NF-κB and an interferon regulatory factor (an impulse response function). As such, a variety of cellular responses are induced, including the production of interferons, proinflammatory cytokines and effector cytokines, therefore promoting immune responses. 13 Toll like receptors have been found in mammals so far. Toll like receptors 1, 2, 4, 5 and 6 are mainly expressed on cellular surfaces and Toll like receptors 3, 7, 8 and 9 are expressed in endosomes. Different toll like receptors recognize ligands derived from different pathogens. Toll like receptor 7 (TLR7) is mainly expressed in plasmacytoid dendritic cells (pDCs), and induces secretion of the interferon alpha (IFN-alpha) by ligand recognition. Some TLR7 agonists have been reported, for example, imiquimod, resiquimod, GS-9620 and the like. WO2016023511 and WO2017076346, which are incorporated herein by reference in their entireties, disclose a class of novel TLR7 agonists exhibiting good bioactivity and selectivity.

The role of TLR7 in tumors has been studied. Imiquimod is a TLR7 agonist approved by US FDA for treating external genital warts, actinic ketatosis and superficial basal cell carcinoma. Imiquimod can promote immune responses of the body, and also can be used as an adjuvant to enhance the efficacy of radiotherapy. However, TLR7 agonists are not suitable to all tumors.

Although patients suffered from proliferative diseases (for example, cancers) have many treatment options, there is still a need for more effective therapeutic agents for clinical uses, in particular combined uses of more than one drug.

SUMMARY

In one aspect, the present application provides a compound of formula I or a pharmaceutically acceptable salt thereof for use in treating lung cancer, or a pharmaceutical composition comprising a compound of formula I or a pharmaceutically acceptable salt thereof for use in treating lung cancer.

In another aspect, the present application further provides a use of a compound of formula I or a pharmaceutically acceptable salt thereof in the preparation of a medicament for treating lung cancer. The present application further provides a method for treating lung cancer, comprising administering to a subject in need thereof an effective amount of a compound of formula I or a pharmaceutically acceptable salt thereof. The present application further provides a use of a compound of formula I or a pharmaceutically acceptable salt thereof for treating lung cancer.

In a second aspect, the present application provides a pharmaceutical combination comprising a TLR7 agonist and anlotinib.

In another aspect, the present application further provides a use of the pharmaceutical combination in the preparation of a medicament for treating lung cancer. The present application further provides a method for treating lung cancer, comprising administering to a subject in need thereof an effective amount of the pharmaceutical combination. The present application further provides the pharmaceutical combination for use in treating lung cancer. The present application further provides a use of the pharmaceutical combination for treating lung cancer. The pharmaceutical combination comprises a TLR7 agonist and anlotinib.

DETAILED DESCRIPTION

In one aspect, the present application provides a compound of formula I or a pharmaceutically acceptable salt thereof for use in treating lung cancer, or a pharmaceutical composition comprising a compound of formula I or a pharmaceutically acceptable salt thereof for use in treating lung cancer, wherein the compound of formula I is shown as follows:

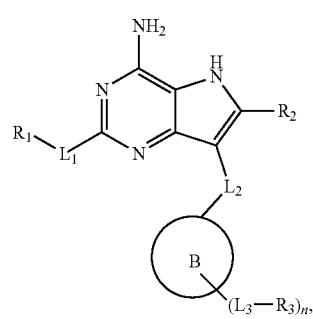

wherein,

L$_1$ and L$_2$ are each independently selected from the group consisting of —O—, —CH$_2$—, —S—, —NH—, —NHC(=O)—, —C(=O)—, —C(=O)NH—, —S(=O)—, —S(=O)$_2$—, —NHS(=O)$_2$— and —S(=O)$_2$NH—, wherein the —CH$_2$—, —NH—, —NHC(=O)—, —C(=O)NH—, —NHS(=O)$_2$— or —S(=O)$_2$NH— is optionally substituted by one or more R$_4$;

R$_1$ is selected from the group consisting of hydrogen, C$_{1-10}$ alkyl, C$_{2-10}$ alkenyl, C$_{2-10}$ alkynyl, C$_{3-10}$ cyclohydrocarbyl, 3-10 membered heterocyclohydrocarbyl, 3-10 membered aryl and 3-10 membered heteroaryl, wherein the C$_{1-10}$ alkyl, C$_{2-10}$ alkenyl, C$_{2-10}$ alkynyl, C$_{3-10}$ cyclohydrocarbyl, 3-10 membered heterocyclohydrocarbyl, 3-10 membered aryl and 3-10 membered heteroaryl are optionally substituted by one or more R$_4$;

R$_2$ is selected from the group consisting of hydrogen, halogen, cyano, hydroxyl, mercapto, amino, —COOH, —CONH$_2$, C$_{1-10}$ alkyl, C$_{2-10}$ alkenyl, C$_{2-10}$ alkynyl, C$_{3-10}$ cyclohydrocarbyl, 3-10 membered heterocyclohydrocarbyl, 3-10 membered aryl and 3-10 membered heteroaryl, wherein the hydroxyl, mercapto, amino, —COOH, —CONH$_2$, C$_{1-10}$ alkyl, C$_{2-10}$ alkenyl, C$_{2-10}$ alkynyl, C$_{3-10}$ cyclohydrocarbyl, 3-10 membered heterocyclohydrocarbyl, 3-10 membered aryl and 3-10 membered heteroaryl are optionally substituted by one or more R$_4$;

B is selected from the group consisting of C$_{3-10}$ cyclohydrocarbyl, 3-10 membered heterocyclohydrocarbyl, 3-10 membered aryl and 3-10 membered heteroaryl;

L$_3$ is selected from the group consisting of a bond, C$_{0-6}$ alkylene, imino, —O—, —S—, —S(=O)— and —S(=O)$_2$—, wherein the C$_{0-6}$ alkylene and imino are optionally substituted by one or more R$_4$;

R$_3$ is selected from the group consisting of hydrogen, amino, C$_{1-10}$ alkyl, C$_{2-10}$ alkenyl, C$_{2-10}$ alkynyl, C$_{3-10}$ cyclohydrocarbyl, 3-10 membered heterocyclohydrocarbyl, 3-10 membered aryl and 3-10 membered heteroaryl, wherein the amino, C$_{1-10}$ alkyl, C$_{2-10}$ alkenyl, C$_{2-10}$ alkynyl, C$_{3-10}$ cyclohydrocarbyl, 3-10 membered heterocyclohydrocarbyl, 3-10 membered aryl and 3-10 membered heteroaryl are optionally substituted by one or more R$_4$, or R$_3$ and L$_3$ together with an adjacent atom on ring B form a saturated or unsaturated 5-8 membered ring which is optionally substituted by one or more R$_4$;

n is 0, 1, 2, 3, 4 or 5;

R$_4$ is selected from the group consisting of halogen, cyano, —R, —OR, =O, —SR, —NR$_2$, =NR, —C(halogen)$_3$, —CR(halogen)$_2$, —CR$_2$(halogen), —OCN, —SCN, —N=C=O, —NCS, —NO, —NO$_2$, —NRC(=O)R, —NRC(=O)OR, —NRC(=O)NRR, —C(=O)NRR, —C(=O)OR, —OC(=O)NRR, —OC(=O)OR, —C(=O)R, —S(=O)$_2$OR, —S(=O)$_2$R, —OS(=O)$_2$OR, —S(=O)$_2$NRR, —S(=O)R, —NRS(=O)$_2$R, —NRS(=O)$_2$NRR, —NRS(=O)$_2$OR, —OP(=O)(OR)$_2$, —P(=O)(OR)$_2$, —C(=O)R, —C(=S)R, —C(=O)OR, —C(=S)OR, —C(=O)SR, —C(=S)SR, —C(=O)NRR, —C(=S)NRR, —C(=NR)NRR and —NRC(=NR)NRR;

each R is independently selected from the group consisting of H, C$_{1-8}$ alkyl, C$_{3-8}$ cyclohydrocarbyl, 3-8 membered heterocyclohydrocarbyl, 3-8 membered aryl, 3-8 membered heteroaryl, 3-8 membered arylalkyl and 3-8 membered heteroarylalkyl; and when L$_1$ is —CH$_2$— or —NH—, R$_3$ is not H;

or a pharmaceutically acceptable salt thereof.

In some embodiments of the present application, the compound of formula I or the pharmaceutically acceptable salt thereof may have one of structures as shown as follows.

In some embodiments of the compound of formula I, L$_1$ and L$_2$ are each independently selected from the group consisting of —O—, —CH$_2$—, —S—, —NH—, —C(=O)—, —S(=O)— and —S(=O)$_2$—, wherein the —CH$_2$— and —NH— are optionally substituted by one or more R$_4$. In some embodiments of the compound of formula I, L$_1$ and L$_2$ are each independently selected from the group consisting of —O—, —CH$_2$—, —S—, and —NH—, wherein the —CH$_2$— and —NH— are optionally substituted by one or more R$_4$. In some embodiments of the compound of formula I, L$_1$ and L$_2$ are each independently selected from the group consisting of —O— and —CH$_2$—, wherein the —CH$_2$— is optionally substituted by one or more R$_4$.

In some embodiments of the compound of formula I, R$_1$ is selected from the group consisting of hydrogen, C$_{1-6}$ alkyl, C$_{2-6}$ alkenyl, C$_{2-6}$ alkynyl, C$_{3-6}$ cyclohydrocarbyl, 3-6 membered heterocyclohydrocarbyl, 3-6 membered aryl and 3-6 membered heteroaryl, wherein the C$_{1-6}$ alkyl, C$_{2-6}$ alkenyl, C$_{2-6}$ alkynyl, C$_{3-6}$ cyclohydrocarbyl, 3-6 membered heterocyclohydrocarbyl, 3-6 membered aryl and 3-6 membered heteroaryl are optionally substituted by one or more R$_4$. In some embodiments of the compound of formula I, R$_1$ is C$_{1-6}$ alkyl, wherein the C$_{1-6}$ alkyl is optionally substituted by one or more R$_4$.

In some embodiments of the compound of formula I, R$_2$ is selected from the group consisting of hydrogen, halogen, cyano, hydroxyl, mercapto, amino, —COOH, —CONH$_2$, C$_{1-6}$ alkyl, C$_{2-6}$ alkenyl, C$_{2-6}$ alkynyl, C$_{3-6}$ cyclohydrocarbyl, 3-6 membered heterocyclohydrocarbyl, 3-6 membered aryl and 3-6 membered heteroaryl, wherein the hydroxyl, mercapto, amino, —COOH, —CONH$_2$, C$_{1-6}$ alkyl, C$_{2-6}$ alkenyl, C$_{2-6}$ alkynyl, C$_{3-6}$ cyclohydrocarbyl, 3-6 membered heterocyclohydrocarbyl, 3-6 membered aryl and 3-6 membered heteroaryl are optionally substituted by one or more R$_4$. In some embodiments of the compound of formula I, R$_2$ is selected from the group consisting of hydrogen, halogen, cyano, hydroxyl, amino, —CONH$_2$ and C$_{1-6}$ alkyl, wherein the hydroxyl, amino, —CONH$_2$ and C$_{1-6}$ alkyl are optionally substituted by one or more R$_4$. In some embodiments of the compound of formula I, R$_2$ is selected from the group consisting of hydrogen, cyano and —CONH$_2$, wherein the —CONH$_2$ is optionally substituted by one or more R$_4$.

In some embodiments of the compound of formula I, B is selected from the group consisting of 3-10 membered aryl and 3-10 membered heteroaryl. In some embodiments of the compound of formula I, B is selected from the group consisting of 5-7 membered aryl and 5-7 membered heteroaryl. In some embodiments of the compound of formula I, B is selected from the group consisting of phenyl, pyridinyl, pyrimidinyl, pyridazinyl, pyrazinyl, thienyl, thiazolyl, furanyl, oxazolyl, thiadiazolyl, isoxazolyl, oxadiazolyl, pyrrolyl, imidazolyl, pyrazolyl, isothiazolyl and triazolyl. In some embodiments of the compound of formula I, B is selected from the group consisting of phenyl, pyridinyl and thiazolyl.

In some embodiments of the compound of formula I, L$_3$ is selected from the group consisting of a bond and C$_{0-6}$ alkylene, wherein the C$_{0-6}$ alkylene is optionally substituted by one or more R$_4$.

In some embodiments of the compound of formula I, R$_3$ is selected from the group consisting of hydrogen, amino, C$_{1-6}$ alkyl, C$_{2-6}$ alkenyl, C$_{2-6}$ alkynyl, C$_{3-8}$ cyclohydrocarbyl, 3-8 membered heterocyclohydrocarbyl, 3-8 membered aryl and 3-8 membered heteroaryl, wherein the amino, $C_{1-6}$ alkyl, $C_{2-6}$ alkenyl, $C_{2-6}$ alkynyl, $C_{3-8}$ cyclohydrocarbyl, 3-8 membered heterocyclohydrocarbyl, 3-8 membered aryl and 3-8 membered heteroaryl are optionally substituted by one or more $R_4$; or $R_3$ and $L_3$ together with an adjacent atom on ring B form a saturated or unsaturated 5-8 membered ring which is optionally substituted by one or more $R_4$. In some embodiments of the compound of formula I, $R_3$ is selected from the group consisting of hydrogen, amino, $C_{1-6}$ alkyl, $C_{3-8}$ cyclohydrocarbyl, 3-8 membered heterocyclohydrocarbyl, 3-8 membered aryl and 3-8 membered heteroaryl, wherein the amino, $C_{1-6}$ alkyl, $C_{3-8}$ cyclohydrocarbyl, 3-8 membered heterocyclohydrocarbyl, 3-8 membered aryl and 3-8 membered heteroaryl are optionally substituted by one or more $R_4$; or $R_3$ and $L_3$ together with an adjacent atom on ring B form a saturated or unsaturated 5-8 membered ring which is optionally substituted by one or more $R_4$. In some embodiments of the compound of formula I, $R_3$ is selected from the group consisting of hydrogen, amino, $C_{1-6}$ alkyl, piperazinyl, morpholinyl, tetrahydropyrrolyl, piperidinyl, azetidinyl, diazepanyl and 2-oxa-5-azabicyclo[2.2.1]heptyl, wherein the amino, $C_{1-6}$ alkyl, piperazinyl, morpholinyl, tetrahydropyrrolyl, piperidinyl, azetidinyl, diazepanyl and 2-oxa-5-azabicyclo[2.2.1]heptyl are optionally substituted by one or more $R_4$; or $R_3$ and $L_3$ together with an adjacent atom on ring B form a saturated or unsaturated 6-membered ring which is optionally substituted by one or more $R_4$.

In some embodiments of the compound of formula I, $R_4$ is selected from the group consisting of halogen, cyano, —R, —OR, =O, —SR, —$NR_2$, =NR, —C(halogen)$_3$, —CR(halogen)$_2$, —$CR_2$(halogen), —OCN, —SCN, —N=C=O, —NCS, —NO, —$NO_2$, —NRC(=O)R, —C(=O)NRR, —C(=O)OR, —OC(=O)NRR, —C(=O)R, —S(=O)$_2$OR, —S(=O)$_2$R, —OS(=O)$_2$OR, —S(=O)$_2$NRR, —S(=O)R, —NRS(=O)$_2$R, —C(=O)R, —C(=O)OR and —C(=O)NRR. In some embodiments of the compound of formula I, $R_4$ is selected from the group consisting of halogen, cyano, —R, —OR, =O, —$NR_2$, =NR, —C(halogen)$_3$, —CR(halogen)$_2$ and —$CR_2$(halogen). In some embodiments of the compound of formula I, $R_4$ is selected from the group consisting of halogen, —R, —OR and =O. In the above embodiments, each R is independently selected from the group consisting of H, $C_{1-8}$ alkyl, $C_{3-8}$ cyclohydrocarbyl, 3-8 membered heterocyclohydrocarbyl, 3-8 membered aryl, 3-8 membered heteroaryl, 3-8 membered arylalkyl and 3-8 membered heteroarylalkyl.

In some embodiments of the present application, the compound of formula I or the pharmaceutically acceptable salt thereof is selected from one or more of the following compounds or pharmaceutically acceptable salts thereof:

2-butoxy-7-(3-((4-methylpiperazin-1-yl)methyl)benzyl)-5H-pyrrolo[3,2-d]pyrimidin-4-amine;
2-butoxy-7-(3-(morpholinomethyl)benzyl)-5H-pyrrolo[3,2-d]pyrimidin-4-amine;
7-(3-(aminomethyl)benzyl)-2-butoxy-5H-pyrrolo[3,2-d]pyrimidin-4-amine;
2-butoxy-7-(3-(pyrrolidin-1-ylmethyl)benzyl)-5H-pyrrolo[3,2-d]pyrimidin-4-amine;
2-butoxy-7-(4-((3,3-difluoropyrrolidin-1-yl)methyl)benzyl)-5H-pyrrolo[3,2-d]pyrimidin-4-amine;
2-butoxy-7-(4-((3-fluoropyrrolidin-1-yl)methyl)benzyl)-5H-pyrrolo[3,2-d]pyrimidin-4-amine;
1-(4-((4-amino-2-butoxy-5H-pyrrolo[3,2-d]pyrimidin-7-yl)methyl)benzyl)pyrrolidin-3-ol;
2-butoxy-7-(4-(piperidin-1-ylmethyl)benzyl)-5H-pyrrolo[3,2-d]pyrimidin-4-amine;
2-butoxy-7-(4-(morpholinomethyl)benzyl)-5H-pyrrolo[3,2-d]pyrimidin-4-amine;
2-butoxy-7-(4-((4-methylpiperazin-1-yl)methyl)benzyl)-5H-pyrrolo[3,2-d]pyrimidin-4-amine;
2-butoxy-7-(4-((dimethylamino)methyl)benzyl)-5H-pyrrolo[3,2-d]pyrimidin-4-amine;
2-butoxy-7-(4-((diethylamino)methyl)benzyl)-5H-pyrrolo[3,2-d]pyrimidin-4-amine;
2-butoxy-7-(4-((dipropylamino)methyl)benzyl)-5H-pyrrolo[3,2-d]pyrimidin-4-amine;
7-(4-(azetidin-1-ylmethyl)benzyl)-2-butoxy-5H-pyrrolo[3,2-d]pyrimidin-4-amine;
2-butoxy-7-(4-((3-methoxyazetidin-1-yl)methyl)benzyl)-5H-pyrrolo[3,2-d]pyrimidin-4-amine;
2-butoxy-7-((4-methyl-1,4-diazepan-1-yl)methyl)benzyl)-5H-pyrrolo[3,2-d]pyrimidin-4-amine;
2-butoxy-7-(4-((2,6-dimethylmorpholino)methyl)benzyl)-5H-pyrrolo[3,2-d]pyrimidin-4-amine;
7-(4-(((1S,4S)-2-oxa-5-azabicyclo[2.2.1]heptan-5-ylmethyl)benzyl)-2-butoxy-5H-pyrrolo[3,2-d]pyrimidin-4-amine;
2-butoxy-7-(4-((4-methoxypiperidin-1-yl)methyl)benzyl)-5H-pyrrolo[3,2-d]pyrimidin-4-amine;
2-butoxy-7-(4-((4-isopropylpiperazin-1-yl)methyl)benzyl)-5H-pyrrolo[3,2-d]pyrimidin-4-amine;
2-butoxy-7-(4-(pyrrolidin-1-ylmethyl)benzyl)-5H-pyrrolo[3,2-d]pyrimidin-4-amine;
2-butoxy-7-((6-pyrolidin-1-ylmethyl)pyridin-3-yl)methyl)-5H-pyrrolo[3,2-d]pyrimidin-4-amine;
2-butoxy-7-(3-(2-(pyrrolidin-1-yl)ethyl)benzyl)-5H-pyrrolo[3,2-d]pyrimidin-4-amine;
2-butoxy-7-(4-(1-(pyrrolidin-1-yl)ethyl)benzyl)-5H-pyrrolo[3,2-d]pyrimidin-4-amine;
2-butoxy-7-(4-(1-methylpiperidin-4-yl)benzyl)-5H-pyrrolo[3,2-d]pyrimidin-4-amine;
2-butoxy-7-(4-(1-methylpyrrolidin-2-yl)benzyl)-5H-pyrrolo[3,2-d]pyrimidin-4-amine;
1-(4-((4-amino-2-butoxy-5H-pyrrolo[3,2-d]pyrimidin-7-yl)methyl)phenyl)-4-methylpiperazin-2-one;
7-benzyl-2-(2-methoxyethoxy)-5H-pyrrolo[3,2-d]pyrimidin-4-amine;
2-(2-methoxyethoxy)-7-((6-methylpyridin-3-yl)methyl)-5H-pyrrolo[3,2-d]pyrimidin-4-amine;
7-((5-chloropyridin-2-yl)methyl)-2-(2-methoxyethoxy)-5H-pyrrolo[3,2-d]pyrimidin-4-amine;
2-(2-methoxyethoxy)-7-((6-(pyrrolidin-1-ylmethyl)pyridin-3-yl)methyl)-5H-pyrrolo[3,2-d]pyrimidin-4-amine;
1-(4-((4-amino-2-(2-methoxyethoxy)-5H-pyrrolo[3,2-d]pyrimidin-7-yl)methyl)phenyl)-4-methylpiperazin-2-one;
4-amino-2-butoxy-7-(4-(pyrolidin-1-ylethyl)benzyl)-5H-pyrrolo[3,2-d]pyrimidin-4-amine,
4-amino-2-butoxy-7-((6-(pyrrolidin-1-ylmethyl)pyridin-3-yl)methyl)-5H-pyrrolo[3,2-d]pyrimidin-6-carbonitrile;
4-amino-2-butoxy-7-(pyrrolidin-1-ylmethyl)benzyl)-5H-pyrrolo[3,2-d]pyrimidin-6-carbonitrile;
4-amino-2-butoxy-7-(4-(morpholinomethyl)benzyl)-5H-pyrrolo[3,2-d]pyrimidin-6-carbonitrile;
4-amino-2-butoxy-7-(4-((4-methylpiperazin-1-yl)methyl)benzyl)-5H-pyrrolo[3,2-d]pyrimidin-6-carbonitrile;
4-amino-2-butoxy-7-(4-(pyrrolidin-1-ylmethyl)benzyl)-5H-pyrrolo[3,2-d]pyrimidin-6-carboxamide;
2-butoxy-7-((1,2,3,4-tetrahydroisoquinolin-7-yl)methyl)-5H-pyrrolo[3,2-d]pyrimidin-4-amine;
2-butoxy-7-((2-methyl-1,2,3,4-tetrahydroisoquinolin-7-yl)methyl)-5H-pyrrolo[3,2-d]pyrimidin-4-amine;
2-butoxy-7-((2-ethyl-1,2,3,4-tetrahydroisoquinolin-7-yl)methyl)-5H-pyrrolo[3,2-d]pyrimidin-4-amine;

2-butoxy-7-((2-isopropyl-1,2,3,4-tetrahydroisoquinolin-7-yl)methyl)-5H-pyrrolo[3,2-d]pyrimidin-4-amine;
2-butoxy-7-((1,2,3,4-tetrahydroisoquinolin-6-yl)methyl)-5H-pyrrolo[3,2-d]pyrimidin-4-amine;
2-butoxy-7-((2-methyl-1,2,3,4-tetrahydroisoquinolin-6-yl)methyl)-5H-pyrrolo[3,2-d]pyrimidin-4-amine;
2-butoxy-7-((2-ethyl-1,2,3,4-tetrahydroisoquinolin-6-yl)methyl)-5H-pyrrolo[3,2-d]pyrimidin-4-amine; or
2-butoxy-7-((2-(pyrolidin-1-ylmethyl)thiazol-5-yl)methyl)pyrrolo[3,2-d]pyrimidin-4-amine.

In some embodiments of the present application, the compound of formula I or the pharmaceutically acceptable salt thereof is 2-butoxy-7-(4-(pyrrolidin-1-ylmethyl)benzyl)-5H-pyrrolo [3,2-d]pyrimidin-4-amine or 2-butoxy-7-((2-(pyrrolidin-1-ylmethyl)thiazol-5-yl)methyl)-5H-pyrrolo [3,2-d]pyrimidin-4-amine or a pharmaceutically acceptable salt thereof. In some embodiments of the present application, the compound of formula I or the pharmaceutically acceptable salt thereof is 2-butoxy-7-(4-(pyrrolidin-1-ylmethyl)benzyl)-5H-pyrrolo[3,2-d]pyrimidin-4-amine or a pharmaceutically acceptable salt thereof.

In another aspect, the present application further provides a use of the compound of formula I or the pharmaceutically acceptable salt thereof or a pharmaceutical composition comprising the compound of formula I or the pharmaceutically acceptable salt thereof in the preparation of a medicament for treating lung cancer. The present application further provides a method for treating lung cancer, comprising administering to a subject in need thereof an effective amount of the compound of formula I or the pharmaceutically acceptable salt thereof, or a pharmaceutical composition comprising the compound of formula I or the pharmaceutically acceptable salt thereof. The present application further provides a use of the compound of formula I or the pharmaceutically acceptable salt thereof or a pharmaceutical composition comprising the compound of formula I or the pharmaceutically acceptable salt thereof for treating lung cancer. In some embodiments of the present application, the compound of formula I or the pharmaceutically acceptable salt thereof in the uses and method can form a pharmaceutical combination with anlotinib or a pharmaceutically acceptable salt thereof.

In a second aspect, the present application provides a pharmaceutical combination comprising a TLR7 agonist and anlotinib.

In some embodiments of the present application, the present application provides a pharmaceutical combination comprising a TLR7 agonist and 1 mg/kg/d of anlotinib or a pharmaceutically acceptable salt thereof. In particular, the pharmaceutical combination comprises 20 mg/kg of TLR7 agonist and 1 mg/kg/d of anlotinib or a pharmaceutically acceptable salt thereof.

In some embodiments of the present application, the TLR7 agonist in the pharmaceutical combination in the present application is selected from the group consisting of imiquimod, GSK-2245035, resiquimod, vesatolimod (GS-9620), telratolimod, TMX-202, DSP-0509, RG-7854, loxoribine, and the compound of formula I or the pharmaceutically acceptable salt thereof, wherein the compound of formula I or the pharmaceutically acceptable salt has one or more of the aforementioned structures or is selected from one or more of the aforementioned compounds.

In some embodiments of the present application, the TLR7 agonist in the pharmaceutical combination may be one or more TLR7 agonists. As used herein, the term "more" refers to more than one, for example, two, three, four, five or more. For example, in some embodiments of the present application, the TLR7 agonist is one or any more selected from the group consisting of GSK-2245035, vesatolimod, 2-butoxy-7-(4-(pyrrolidin-1-ylmethyl)benzyl)-5H-pyrrolo[3,2-d]pyrimidin-4-amine, 2-butoxy-7-((2-(pyrrolidin-1-ylmethyl)thiazol-5-yl)methyl)-5H-pyrrolo[3,2-d]pyrimidin-4-amine, and a pharmaceutically acceptable salt thereof.

In some embodiments of the present application, the pharmaceutical combination is a fixed combination. In some embodiments, the fixed combination is in the form of a solid pharmaceutical composition. In some embodiments, the solid pharmaceutical composition is selected from the group consisting of a tablet and a capsule.

In some embodiments of the present application, the pharmaceutical combination is an unfixed combination. In some embodiments, the TLR7 agonist and anlotinib in the unfixed combination are each in the form of a solid pharmaceutical composition. In some embodiments, the solid pharmaceutical composition is selected from the group consisting of a tablet and a capsule.

In some embodiments of the present application, the TLR7 agonist in the pharmaceutical combination is selected from the group consisting of GSK-2245035, vesatolimod, 2-butoxy-7-(4-(pyrrolidin-1-ylmethyl)benzyl)-5H-pyrrolo[3,2-d]pyrimidin-4-amine, 2-butoxy-7-((2-(pyrrolidin-1-ylmethyl)thiazol-5-yl)methyl)-5H-pyrrolo[3,2-d]pyrimidin-4-amine, and a pharmaceutically acceptable salt thereof.

In some embodiments of the present application, the pharmaceutical combination comprises 2-butoxy-7-(4-(pyrrolidin-1-ylmethyl)benzyl)-5H-pyrrolo[3,2-d]pyrimidin-4-amine or 2-butoxy-7-((2-(pyrrolidin-1-ylmethyl)thiazol-5-yl)methyl)-5H-pyrrolo[3,2-d]pyrimidin-4-amine, or a pharmaceutically acceptable salt thereof, and anlotinib or a pharmaceutically acceptable salt thereof.

In some embodiments of the present application, the pharmaceutical combination in the present application comprises 2-butoxy-7-(4-(pyrrolidin-1-ylmethyl)benzyl)-5H-pyrrolo[3,2-d]pyrimidin-4-amine or a pharmaceutically acceptable salt thereof, and anlotinib dihydrochloride.

In some embodiments of the present application, the pharmaceutical combination in the present application comprises 0.0001 mg/kg/d to 20 mg/kg/d of 2-butoxy-7-(4-(pyrrolidin-1-ylmethyl) benzyl)-5H-pyrrolo[3,2-d]pyrimidin-4-amine or a pharmaceutically acceptable salts thereof, and 1 mg/kg/d of anlotinib dihydrochloride. In some embodiments of the present application, the pharmaceutical combination in the present application comprises 0.001 mg/kg/d to 10 mg/kg/d of 2-butoxy-7-(4-(pyrrolidin-1-ylmethyl)benzyl)-5H-pyrrolo[3,2-d]pyrimidin-4-amine or a pharmaceutically acceptable salt thereof, and 1 mg/kg/d of anlotinib dihydrochloride. In some embodiments of the present application, the pharmaceutical combination in the present application comprises 0.0001 mg/kg/d to 20 mg/kg/d of 2-butoxy-7-(4-(pyrrolidin-1-ylmethyl)benzyl)-5H-pyrrolo[3,2-d]pyrimidin-4-amine or a pharmaceutically acceptable salt thereof, and anlotinib dihydrochloride at a dosage of 6 mg, 8 mg, 10 mg or 12 mg once daily. In some embodiments of the present application, the pharmaceutical combination in the present application comprises 0.001 mg/kg/d to 10 mg/kg/d of 2-butoxy-7-(4-(pyrrolidin-1-ylmethyl)benzyl)-5H-pyrrolo[3,2-d]pyrimidin-4-amine or a pharmaceutically acceptable salt thereof, and anlotinib dihydrochloride at a dosage of 6 mg, 8 mg, 10 mg or 12 mg once daily. In some embodiments of the present application, the pharmaceutical combination in the present application comprises 20 mg/kg/d of 2-butoxy-7-(4-(pyrrolidin-1-ylmethyl)benzyl)-5H-pyrrolo[3,2-d]pyrimidin-4-amine and 1 mg/kg/d of anlotinib dihydrochloride. In some embodiments of the present application, the pharmaceutical combination in the present application comprises 0.0001 mg/kg/dose to 20 mg/kg/dose of 2-butoxy-7-(4-(pyrrolidin-1-ylmethyl)benzyl)-5H-pyrrolo[3,2-d]pyrimidin-4-amine or a pharmaceutically acceptable salt thereof administered thrice weekly, and 1 mg/kg/d of anlotinib dihydrochloride administered for 11 days continuously. In some embodiments of the present application, the pharmaceutical combination in the present application comprises 0.001 mg/kg/dose to 10 mg/kg/dose of 2-butoxy-7-(4-(pyrrolidin-1-ylmethyl)benzyl)-5H-pyrrolo[3,2-d]pyrimidin-4-amine or a pharmaceutically acceptable salt thereof administered thrice weekly, and 1 mg/kg/d of anlotinib dihydrochloride administered for 11 days continuously. In some embodiments of the present application, the pharmaceutical combination in the present application comprises 0.0001 mg/kg/dose to 20 mg/kg/dose of 2-butoxy-7-(4-(pyrrolidin-1-ylmethyl)benzyl)-5H-pyrrolo [3,2-d]pyrimidin-4-amine or a pharmaceutically acceptable salt thereof administered thrice weekly, and anlotinib dihydrochloride administered for 11 days continuously at a dosage of 6 mg, 8 mg, 10 mg or 12 mg once daily. In some embodiments of the present application, the pharmaceutical combination in the present application comprises 0.001 mg/kg/dose to 10 mg/kg/dose of 2-butoxy-7-(4-(pyrrolidin-1-ylmethyl) benzyl)-5H-pyrrolo[3,2-d]pyrimidin-4-amine or a pharmaceutically acceptable salt thereof administered thrice weekly, and anlotinib dihydrochloride administered for 11 days continuously at a dosage of 6 mg, 8 mg, 10 mg or 12 mg once daily. In some embodiments of the present application, the pharmaceutical combination in the present application comprises 20 mg/kg/dose of 2-butoxy-7-(4-(pyrrolidin-1-ylmethyl)benzyl)-5H-pyrrolo[3,2-d]pyrimidin-4-amine administered thrice weekly, and 1 mg/kg/d of anlotinib dihydrochloride administered for 11 days continuously.

In another aspect, the present application further provides a use of the pharmaceutical combination in the present application in the preparation of a medicament for treating lung cancer. The present application further provides a method for treating lung cancer, comprising administering to a subject in need thereof an effective amount of the pharmaceutical combination in the present application. The present application further provides the pharmaceutical combination in the present application for use in treating lung cancer. The present application further provides a use of the pharmaceutical combination in the present application for treating lung cancer. The pharmaceutical combination comprises a TLR7 agonist and anlotinib. In some embodiments of the present application, the TLR7 agonist is selected from the group consisting of imiquimod, GSK-2245035, resiquimod, vesatolimod (GS-9620), telratolimod, TMX-202, DSP-0509, RG-7854, loxoribine, and the compound of formula I or the pharmaceutically acceptable salt thereof, wherein the compound of formula I or the pharmaceutically acceptable salt has one or more of the aforementioned structures or is selected from one or more of the aforementioned compounds. In some embodiments of the present application, the TLR7 agonist is selected from one or any more of GSK-2245035, vesatolimod, and 2-butoxy-7-(4-(pyrrolidin-1-ylmethyl)benzyl)-5H-pyrrolo[3,2-d]pyrimidin-4-amine or 2-butoxy-7-((2-(pyrrolidin-1-ylmethyl)thiazol-5-yl)methyl)-5H-pyrrolo[3,2-d]pyrimidin-4-amine, or a pharmaceutically acceptable salt thereof. In some embodiments of the present application, the TLR7 agonist is selected from 2-butoxy-7-(4-(pyrrolidin-1-ylmethyl)benzyl)-5H-pyrrolo[3,2-d]pyrimidin-4-amine, 2-butoxy-7-((2-(pyrrolidin-1-ylmethyl)thiazol-5-yl)methyl)-5H-pyrrolo[3,2-d]pyrimidin-4-amine, or a pharmaceutically acceptable salt thereof. In some embodiments of the present application, the TLR7 agonist is 2-butoxy-7-(4-(pyrrolidin-1-ylmethyl)benzyl)-5H-pyrrolo [3,2-d]pyrimidin-4-amine.

In some embodiments of the present application, the present application provides a use of a TLR7 agonist and anlotinib in the preparation of a combined medicament for treating lung cancer, wherein the TLR7 agonist and anlotinib are formulated into pharmaceutical compositions separately.

In some embodiments of the present application, the present application further provides a kit for treating lung cancer, comprising (a) a first pharmaceutical composition comprising a TLR7 agonist as an active ingredient, and (b) a second pharmaceutical composition comprising anlotinib as an active ingredient.

In some embodiments of the present application, the lung cancer includes small cell lung cancer and non-small cell lung cancer.

Definitions and Description

Unless otherwise stated, the following terms used in the present application shall have the following meanings. A specific term, unless otherwise specifically defined, should not be considered indefinite or unclear, but construed according to its common meaning in the art. When referring to a trade name in the present application, it is intended to refer to its corresponding commercial product or its active ingredient.

As used herein, anlotinib has a chemical name of 1-[[[4-(4-fluoro-2-methyl-1H-indol-5-yl)oxy-6-methoxyquinolin-7-yl]oxy]methyl]cyclopropylamine, and the following structural formula:

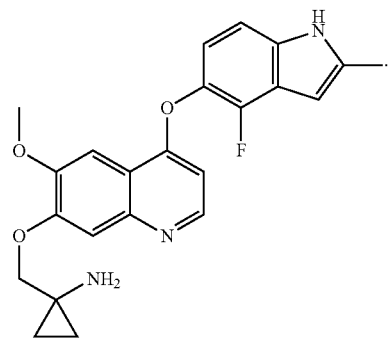

As used herein, the names, structural formulae and chemical names of part of the TLR7 agonists are shown in the following table.

| Name/No. | Structural formula | Chemical name |
|---|---|---|
| 1 | 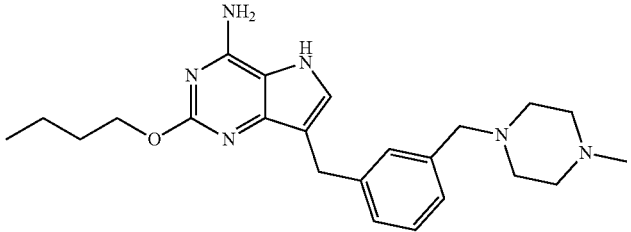 [SMILES: CCCCOc1nc(N)c2[nH]cc(Cc3cccc(CN4CCN(C)CC4)c3)c2n1] | 2-butoxy-7-(3-((4-methylpiperazin-1-yl)methyl)benzyl)-5H-pyrrolo[3,2-d]pyrimidin-4-amine |
| 2 | 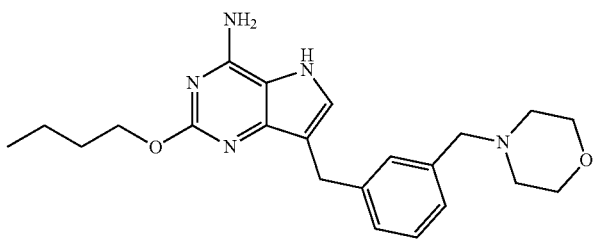 [SMILES: CCCCOc1nc(N)c2[nH]cc(Cc3cccc(CN4CCOCC4)c3)c2n1] | 2-butoxy-7-(3-(morpholinomethyl)benzyl)-5H-pyrrolo[3,2-d]pyrimidin-4-amine |
| 3 | 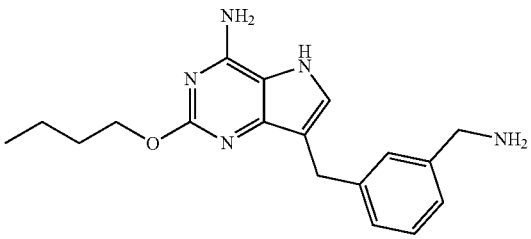 [SMILES: CCCCOc1nc(N)c2[nH]cc(Cc3cccc(CN)c3)c2n1] | 7-(3-(aminomethyl)benzyl)-2-butoxy-5H-pyrrolo[3,2-d]pyrimidin-4-amine |
| 4 | 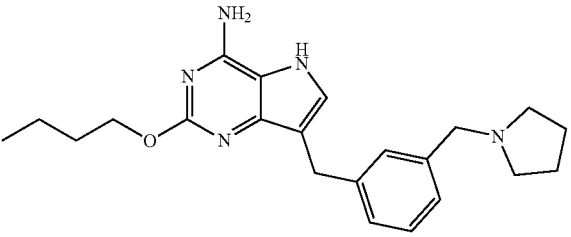 [SMILES: CCCCOc1nc(N)c2[nH]cc(Cc3cccc(CN4CCCC4)c3)c2n1] | 2-butoxy-7-(3-(pyrrolidin-1-ylmethyl)benzyl)-5H-pyrrolo[3,2-d]pyrimidin-4-amine |
| 5 | 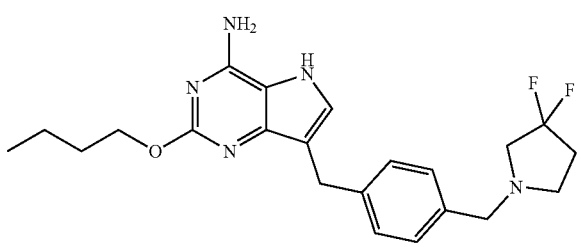 [SMILES: CCCCOc1nc(N)c2[nH]cc(Cc3ccc(CN4CCC(F)(F)C4)cc3)c2n1] | 2-butoxy-7-(4-((3,3-difluoropyrrolidin-1-yl)methyl)benzyl)-5H-pyrrolo[3,2-d]pyrimidin-4-amine |
| 6 | 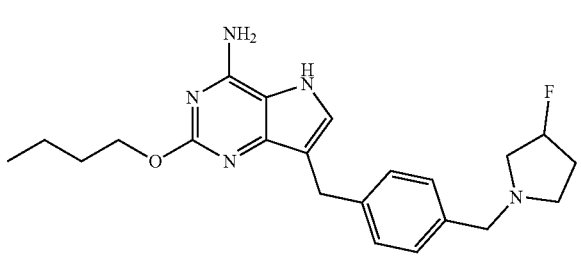 [SMILES: CCCCOc1nc(N)c2[nH]cc(Cc3ccc(CN4CCC(F)C4)cc3)c2n1] | 2-butoxy-7-(4-((3-fluoropyrrolidin-1-yl)methyl)benzyl)-5H-pyrrolo[3,2-d]pyrimidin-4-amine |

-continued

| Name/No. | Structural formula | Chemical name |
|---|---|---|
| 7 | 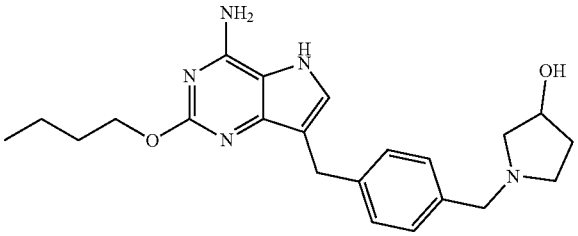 [SMILES: CCCCOc1nc(N)c2[nH]cc(Cc3ccc(CN4CCC(O)C4)cc3)c2n1] | 1-(4-((4-amino-2-butoxy-5H-pyrrolo[3,2-d]pyrimidin-7-yl)methyl)benzyl)pyrrolidin-3-ol |
| 8 | 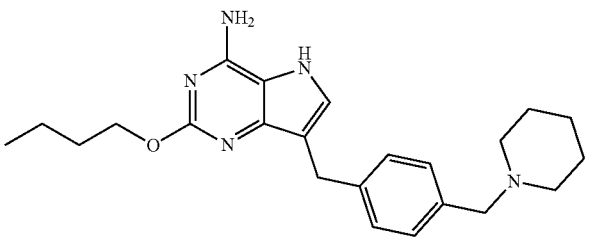 [SMILES: CCCCOc1nc(N)c2[nH]cc(Cc3ccc(CN4CCCCC4)cc3)c2n1] | 2-butoxy-7-(4-(piperidin-1-ylmethyl)benzyl)-5H-pyrrolo[3,2-d]pyrimidin-4-amine |
| 9 | 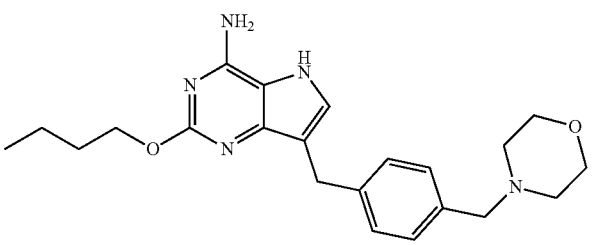 [SMILES: CCCCOc1nc(N)c2[nH]cc(Cc3ccc(CN4CCOCC4)cc3)c2n1] | 2-butoxy-7-(4-(morpholinomethyl)benzyl)-5H-pyrrolo[3,2-d]pyrimidin-4-amine |
| 10 | 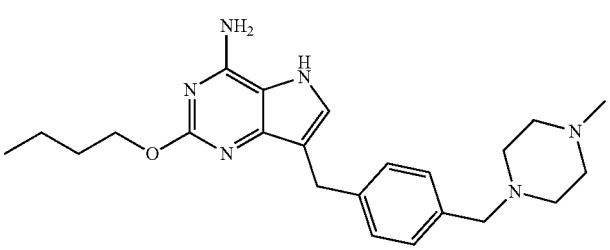 [SMILES: CCCCOc1nc(N)c2[nH]cc(Cc3ccc(CN4CCN(C)CC4)cc3)c2n1] | 2-butoxy-7-(4-((4-methylpiperazin-1-yl)methyl)benzyl)-5H-pyrrolo[3,2-d]pyrimidin-4-amine |
| 11 | 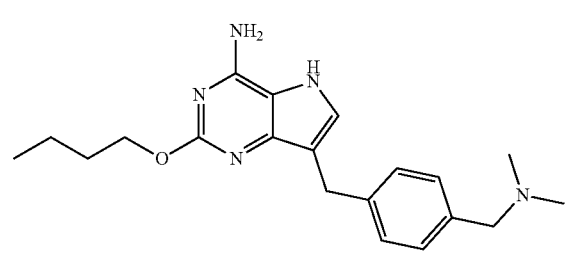 [SMILES: CCCCOc1nc(N)c2[nH]cc(Cc3ccc(CN(C)C)cc3)c2n1] | 2-butoxy-7-(4-((dimethylamino)methyl)benzyl)-5H-pyrrolo[3,2-d]pyrimidin-4-amine |
| 12 | 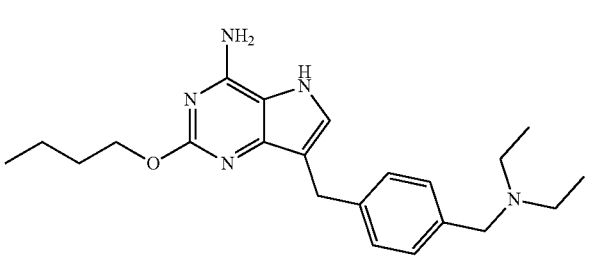 [SMILES: CCCCOc1nc(N)c2[nH]cc(Cc3ccc(CN(CC)CC)cc3)c2n1] | 2-butoxy-7-(4-((diethylamino)methyl)benzyl)-5H-pyrrolo[3,2-d]pyrimidin-4-amine |

-continued

| Name/No. | Structural formula | Chemical name |
|---|---|---|
| 13 | | 2-butoxy-7-(4-((dipropylamino)methyl)benzyl)-5H-pyrrolo[3,2-d]pyrimidin-4-amine |
| 14 | | 7-(4-(azetidin-1-ylmethyl)benzyl)-2-butoxy-5H-pyrrolo[3,2-d]pyrimidin-4-amine |
| 15 | | 2-butoxy-7-(4-((3-methoxyazetidin-1-yl)methyl)benzyl)-5H-pyrrolo[3,2-d]pyrimidin-4-amine |
| 16 | | 2-butoxy-7-(4-((4-methyl-1,4-diazepan-1-yl)methyl)benzyl)-5H-pyrrolo[3,2-d]pyrimidin-4-amine |
| 17 | | 2-butoxy-7-(4-((2,6-dimethylmorpholino)methyl)benzyl)-5H-pyrrolo[3,2-d]pyrimidin-4-amine |
| 18 | | 7-(4-(((1S,4S)-2-oxa-5-azabicyclo[2.2.1]heptan-5-yl)methyl)benzyl)-2-butoxy-5H-pyrrolo[3,2-d]pyrimidin-4-amine |

-continued

| Name/No. | Structural formula | Chemical name |
|---|---|---|
| 19 | | 2-butoxy-7-(4-((4-methoxypiperidin-1-yl)methyl)benzyl)-5H-pyrrolo[3,2-d]pyrimidin-4-amine |
| 20 | | 2-butoxy-7-(4-((4-isopropylpiperazin-1-yl)methyl)benzyl)-5H-pyrrolo[3,2-d]pyrimidin-4-amine |
| 21 | | 2-butoxy-7-(4-(pyrrolidin-1-ylmethyl)benzyl)-5H-pyrrolo[3,2-d]pyrimidin-4-amine |
| 22 | | 2-butoxy-7-((6-(pyrrolidin-1-ylmethyl)pyridin-3-yl)methyl)-5H-pyrrolo[3,2-d]pyrimidin-4-amine |
| 23 | | 2-butoxy-7-(3-(2-(pyrrolidin-1-yl)ethyl)benzyl)-5H-pyrrolo[3,2-d]pyrimidin-4-amine |
| 24 | | 2-butoxy-7-(4-(1-(pyrrolidin-1-yl)ethyl)benzyl)-5H-pyrrolo[3,2-d]pyrimidin-4-amine |

| Name/No. | Structural formula | Chemical name |
|---|---|---|
| 25 | | 2-butoxy-7-(4-(1-methylpiperidin-4-yl)benzyl)-5H-pyrrolo[3,2-d]pyrimidin-4-amine |
| 26 | | 2-butoxy-7-(4-(1-methylpyrrolidin-2-yl)benzyl)-5H-pyrrolo[3,2-d]pyrimidin-4-amine |
| 27 | | 1-(4-((4-amino-2-butoxy-5H-pyrrolo[3,2-d]pyrimidin-7-yl)methyl)phenyl)-4-methylpiperazin-2-one |
| 28 | | 7-benzyl-2-(2-methoxyethoxy)-5H-pyrrolo[3,2-d]pyrimidin-4-amine |
| 29 | | 2-(2-methoxyethoxy)-7-((6-methylpyridin-3-yl)methyl)-5H-pyrrolo[3,2-d]pyrimidin-4-amine |
| 30 | | 7-((5-chloropyridin-2-yl)methyl)-2-(2-methoxyethoxy)-5H-pyrrolo[3,2-d]pyrimidin-4-amine |

-continued

| Name/No. | Structural formula | Chemical name |
|---|---|---|
| 31 | | 2-(2-methoxyethoxy)-7-((6-(pyrrolidin-1-yl methyl)pyridin-3-yl)methyl)-5H-pyrrolo[3,2-d]pyrimidin-4-amine |
| 32 | | 1-(4-((4-amino-2-(2-methoxyethoxyl)-5H-pyrrolo[3,2-d]pyrimidin-7-yl)methyl)phenyl)-4-methylpiperazin-2-one |
| 33 | | 2-butoxy-7-((5-(pyrrolidin-1-ylmethyl)pyridin-2-yl)methyl)-5H-pyrrolo[3,2-d]pyrimidin-4-amine |
| 34 | | 4-amino-2-butoxy-7-((6-(pyrrolidin-1-yl methyl)pyridin-3-yl)methyl)-5H-pyrrolo[3,2-d]pyrimidin-6-carbonitrile |
| 35 | | 4-amino-2-butoxy-7-(4-(pyrrolidin-1-yl methyl)benzyl)-5H-pyrrolo[3,2-d]pyrimidin-6-carbonitrile |
| 36 | | 4-amino-2-butoxy-7-(4-(morpholinomethyl)benzyl)-5H-pyrrolo[3,2-d]pyrimidin-6-carbonitrile |

-continued

| Name/No. | Structural formula | Chemical name |
|---|---|---|
| 37 | | 4-amino-2-butoxy-7-(4-((4-methylpiperazin-1-yl)methyl)benzyl)-5H-pyrrolo[3,2-d]pyrimidin-6-carbonitrile |
| 38 | | 4-amino-2-butoxy-7-(4-(pyrrolidin-1-yl methyl)benzyl)-5H-pyrrolo[3,2-d]pyrimidin-6-carboxamide |
| 39 | | 2-butoxy-7-((1,2,3,4-tetrahydroisoquinolin-7-yl)methyl)-5H-pyrrolo[3,2-d]pyrimidin-4-amine |
| 40 | | 2-butoxy-7-((2-methyl-1,2,3,4-tetrahydro-isoquinolin-7-yl)methyl)-5H-pyrrolo[3,2-d]pyrimidin-4-amine |
| 41 | | 2-butoxy-7-((2-ethyl-1,2,3,4-tetrahydro-isoquinolin-7-yl)methyl)-5H-pyrrolo[3,2-d]pyrimidin-4-amine |
| 42 | | 2-butoxy-7-((2-isopropyl-1,2,3,4-tetrahydro-isoquinolin-7-yl)methyl)-5H-pyrrolo[3,2-d]pyrimidin-4-amine |

-continued

| Name/No. | Structural formula | Chemical name |
|---|---|---|
| 43 | | 2-butoxy-7-((1,2,3,4-tetrahydroisoquinolin-6-yl)methyl)-5H-pyrrolo[3,2-d]pyrimidin-4-amine |
| 44 | | 2-butoxy-7-((2-methyl-1,2,3,4-tetrahydro-isoquinolin-6-yl)methyl)-5H-pyrrolo[3,2-d]pyrimidin-4-amine |
| 45 | | 2-butoxy-7-((2-ethyl-1,2,3,4-tetrahydro-isoquinolin-6-yl)methyl)-5H-pyrrolo[3,2-d]pyrimidin-4-amine |
| 46 | | 2-butoxy-7-((2-(pyrrolidin-1-ylmethyl)thiazol-5-yl)methyl)-5H-pyrrolo[3,2-d]pyrimidin-4-amine |
| Imiquimod | | — |
| GSK-2245035 | | — |

| Name/No. | Structural formula | Chemical name |
|---|---|---|
| Resiquimod | 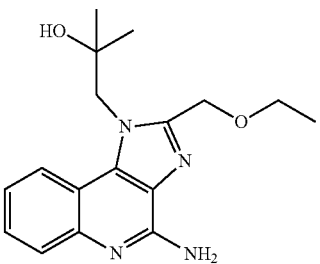 [SMILES: CCOCc1nc2c(N)nc3ccccc3c2n1CC(C)(C)O] | — |
| vesatolimod | 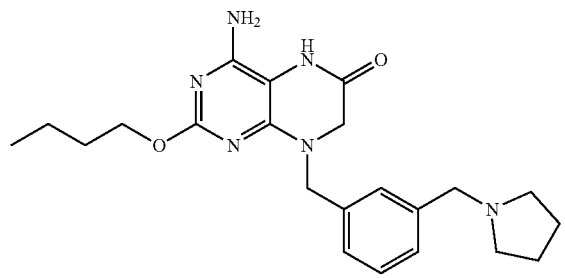 [SMILES: CCCCOc1nc(N)c2c(n1)N(Cc1cccc(CN3CCCC3)c1)CC(=O)N2] | — |
| telratolimod | 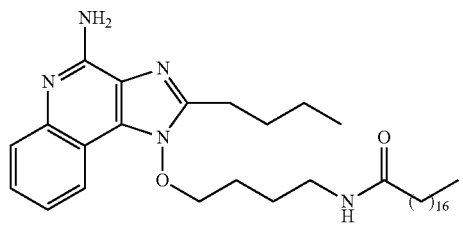 | — |
| TMX-202 | 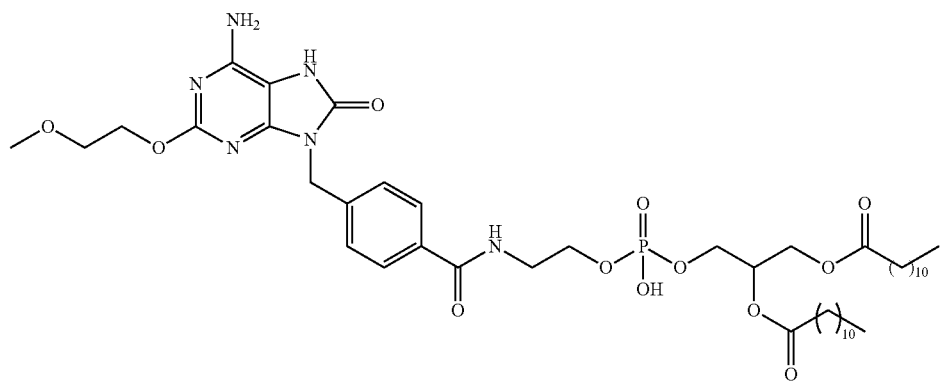 | — |
| DSP-0509 | — | — |
| RG-7854 | — | — |

| Name/No. | Structural formula | Chemical name |
|---|---|---|
| Loxoribine | ![Loxoribine structure] | — |

The terms "substitute" and "substituted" mean that any one or more hydrogen atoms on a specific atom are replaced with substituents, as long as the valence state of the specific atom is normal and the resulting compound after substitution is stable. When the substituent is an oxo (namely =O), it means that two hydrogen atoms are replaced, and the oxo substitution will not occur on an aromatic group.

The terms "optional" and "optionally" mean that the subsequently described event or circumstance may or may not occur. The description includes instances where said event or circumstance occurs and instances where said event or circumstance does not occur. For example, an ethyl is optionally substituted by halogen, which means that the ethyl may be unsubstituted ($CH_2CH_3$), mono-substituted (for example, $CH_2CH_2F$), multiple-substituted (for example, $CHFCH_2F$, $CH_2CHF_2$ and the like) or fully substituted ($CF_2CF_3$). It will be appreciated by those skilled in the art that for any groups comprising one or more substituents, any substitutions or substitution modes that are spatially impossible and/or not synthesizable will not be introduced.

The expression $C_{m-n}$ as used herein means that this moiety has an integer number of carbon atoms within the given range. For example, "$C_{1-6}$" means that this group may have 1 carbon atom, 2 carbon atoms, 3 carbon atoms, 4 carbon atoms, 5 carbon atoms or 6 carbon atoms.

When any variable (e.g., R) occurs more than one time in the composition or structure of a compound, the variable is defined independently at each occurrence. Therefore, for example, if a group is substituted by two Rs, then each R has an independent option.

When the number of a linking group is 0, for example, —$(CH_2)_0$—, it means that the linking group is a covalent bond.

When a bond of a substituent is cross-linked to two atoms on a ring, the substituent may be bonded to any atom on the ring. For example, a structural unit

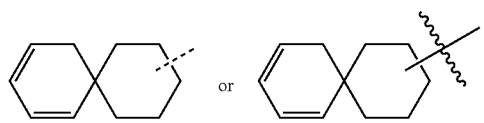

means it may be substituted at any position on cyclohexyl or cyclohexadiene.

The terms "halo-", "halogenated" or "halogen" refer to fluoro, chloro, bromo and iodo.

The term "hydroxyl" refers to —OH group.
The term "cyano" refers to —CN group.
The term "mercapto" refers to —SH group.
The term "amino" refers to —$NH_2$ group.
The term "alkyl" refers to a hydrocarbon group of Formula $C_nH_{2n+1}$. The alkyl group can be straight or branched. For example, the term "$C_1$-$C_6$ alkyl" refers to an alkyl group having 1 to 6 carbon atoms (such as methyl, ethyl, n-propyl, isopropyl, n-butyl, isobutyl, sec-butyl, tert-butyl, n-pentyl, 1-methylbutyl, 2-methylbutyl, 3-methylbutyl, neopentyl, hexyl, 2-methylpentyl, etc.). Similarly, the alkyl moiety (i.e., alkyl) in an alkoxy group, a monoalkylamino group, a dialkylamino group, an alkylsulfonyl group, and an alkylthio group has the same definition as defined above.

The term "alkoxy" refers to —O-alkyl.
The term "alkenyl" refers to a straight or branched unsaturated aliphatic hydrocarbon group consisting of carbon atoms and hydrogen atoms, which has at least one double bond. Non-limiting examples of alkenyl groups include, but are not limited to, ethenyl, 1-propenyl, 2-propenyl, 1-butenyl, isobutenyl, 1,3-butadienyl, and the like.

The term "alkynyl" means a straight or branched unsaturated aliphatic hydrocarbon group consisting of carbon atoms and hydrogen atoms, which has at least one triple bond. Non-limiting examples of alkynyl groups include, but are not limited to, ethynyl (—C≡CH), 1-propynyl (—C≡C—$CH_3$), 2-propynyl (—$CH_2$—C≡CH), 1,3-butadiynyl (—C≡C—C≡CH), and the like.

The term "cycloalkyl" refers to a fully saturated carbocycle that can exist in the form of a monocycle, bridged cycle or spiro cycle. Unless otherwise indicated, the carbocycle is typically a 3-to 10-membered ring. Non-limiting examples of cycloalkyl includes, but are not limited to, cyclopropyl, cyclobutyl, cyclopentyl, cyclohexyl, norbornyl (bicyclo[2.2.1]heptyl), bicyclo[2.2.2]octyl, adamantyl and the like.

The term "cyclohydrocarbyl" refers to a saturated or unsaturated nonaromatic cyclic hydrocarbon group consisting of carbon atoms and hydrogen atoms, preferably including 1 or 2 rings. The cyclohydrocarbyl can be of monocyclic, fused polycyclic, bridged cyclic or spiro cyclic structure. Non-limiting examples of cyclohydrocarbyl include, but are not limited to, cyclopropyl, cyclobutyl, cyclopentyl, cyclohexyl, cycloheptyl, bicyclo[2.2.1]heptyl, spiro[3.3]heptyl and the like.

The term "heterocyclyl" refers to a fully saturated or partially unsaturated (but not fully unsaturated aromatic) nonaromatic cycle that can exist in the form of a monocycle, fused polycycle, bridged cycle or spiro cycle. Unless otherwise indicated, the heterocycle is typically a 3- to 7-membered ring containing 1 to 3 heteroatoms (preferably 1 or 2 heteroatoms) independently selected from sulfur, oxygen and/or nitrogen. Non-limiting examples of heterocyclyl include, but are not limited to, oxiranyl, tetrahydrofuranyl, dihydrofuranyl, pyrrolidinyl, N-methylpyrrolidinyl, dihydropyrrolyl, piperidinyl, piperazinyl, pyrazolidinyl, 4H-pyranyl, morpholinyl, thiomorpholinyl, tetrahydrothienyl and the like.

The term "heterocycloalkyl" refers to a fully saturated cyclic group that can exist in the form of a monocycle, fused polycycle, bridged cycle or spiro cycle. Unless otherwise indicated, the heterocycle is typically a 3- to 7-membered ring containing 1 to 3 heteroatoms (preferably 1 or 2 heteroatoms) independently selected from sulfur, oxygen and/or nitrogen. Examples of 3-membered heterocycloalkyl include, but are not limited to, oxiranyl, thiiranyl, and aziridinyl. Non-limiting examples of 4-membered heterocycloalkyl include, but are not limited to, azetidinyl, oxetanyl, and thietanyl. Examples of 5-membered heterocycloalkyl include, but are not limited to, tetrahydrofuranyl, tetrahydrothiophenyl, pyrrolidinyl, isoxazolidinyl, oxazolidinyl, isothiazolidinyl, thiazolidinyl, imidazolidinyl, and tetrahydropyrazolyl. Examples of 6-membered heterocycloalkyl include, but are not limited to, piperidinyl, tetrahydropyranyl, tetrahydrothiopyranyl, morpholinyl, piperazinyl, 1,4-oxathianyl, 1,4-dioxanyl, thiomorpholinyl, 1,3-dithianyl, and 1,4-dithianyl. Examples of 7-membered heterocycloalkyl include, but are not limited to azepanyl, oxepanyl, and thiepanyl. The preferred heterocycloalkyl is a monocyclic heterocycloalkyl group having 5 or 6 ring atoms.

The term "heterocyclohydrocarbyl" refers to a nonaromatic monocyclic, fused polycyclic, bridged cyclic or spiro cyclic group, wherein some ring atoms are heteroatoms selected from N, O, and S(O). (n is 0, 1 or 2), and the remaining ring atoms are C. Such a ring can be saturated or unsaturated (for example, with one or more double bonds), but does not have a fully conjugated 7-electron system. Examples of 3-membered heterocyclohydrocarbyl include, but are not limited to, oxiranyl, thiiranyl, and aziridinyl. Examples of 4-membered heterocyclohydrocarbyl include, but are not limited to, azetidinyl, oxetanyl, and thietanyl. Examples of 5-membered heterocyclohydrocarbyl include, but are not limited to, tetrahydrofuranyl, tetrahydrothiophenyl, pyrrolidinyl, isoxazolidinyl, oxazolidinyl, isothiazolidinyl, 1,1-dioxoisothiazolidinyl, thiazolidinyl, imidazolidinyl, tetrahydropyrazolyl, pyrrolinyl, dihydrofuranyl and dihydrothienyl. Examples of 6-membered heterocyclohydrocarbyl include, but are not limited to, piperidinyl, tetrahydropyranyl, tetrahydrothiopyranyl, morpholinyl, piperazinyl, 1,4-oxathianyl, 1,4-dioxanyl, thiomorpholinyl, 1,2-dithianyl and 1,4-dithianyl, dihydropyridinyl, tetrahydropyridinyl, dihydropyranyl, tetrahydropyranyl and dihydrothiapyranyl. Examples of 7-membered heterocyclohydrocarbyl include, but are not limited to, azepanyl, oxepanyl, thiepanyl, oxaazabicyclo[2.2.1]heptyl, azaspiro[3.3]heptyl and the like.

The term "aryl" refers to an all-carbon monocyclic or fused polycyclic aromatic ring group having a fully conjugated 7-electron system. For example, an aryl group can have 6-20 carbon atoms, 6-14 carbon atoms or 6-12 carbon atoms. Non-limiting examples of aryl include, but are not limited to, phenyl, naphthyl, anthracenyl, 1,2,3,4-tetrahydronaphthalene, and the like.

The term "heteroaryl" refers to a monocyclic or fused polycyclic system, which contains at least one ring atom selected from the group consisting of N, O and S and the remaining ring atom(s) is(are) C, and has at least one aromatic ring. Preferred heteroaryl groups have a single 4- to 8-membered ring, especially a single 5- to 8-membered ring, or a plurality of fused rings containing 6 to 14, especially 6 to 10 ring atoms. Non-limiting examples of heteroaryl groups include, but are not limited to, pyrrolyl, furyl, thienyl, imidazolyl, oxazolyl, pyrazolyl, pyridyl, pyrimidinyl, pyrazinyl, quinolinyl, isoquinolinyl, tetrazolyl, triazolyl, triazinyl, benzofuranyl, benzothienyl, indolyl, isoindolyl, and the like.

The term "treatment", "treat" or "treating" typically refers to obtaining a desired pharmacological effect and/or physiological effect. The effect may be prophylactic in term of completely or partially preventing a disease or a symptom thereof and/or may be therapeutic in term of a partial or complete stabilization or cure for a disease and/or adverse effect(s) attributable to the disease. "Treatment" as used herein covers any treatment to a disease in a patient, including (a) preventing a disease or a symptom of a disease from occurring in a patient which may be predisposed to the disease but has not yet been diagnosed as suffering from it; (b) inhibiting a symptom of a disease, i.e., arresting its development; or (c) relieving a symptom of a disease, i.e., causing regression of a disease or its symptom.

The term "effective amount" means an amount of a compound of the present application that (i) treats or prevents a particular disease, condition, or disorder, (ii) attenuates, ameliorates, or eliminates one or more symptoms of a particular disease, condition, or disorder, or (iii) prevents or retards the onset of one or more symptoms of a particular disease, condition, or disorder as described herein. The amount of the compound of the present application constituting "therapeutically effective amount" depends on the compound, disease condition and severity thereof, the way of administration and age of the mammal to be treated, but can be routinely determined by those skilled in the art on the basis of their knowledge and the disclosure herein.

As used herein, the compound of formula I or the pharmaceutically acceptable salt can be administered by any suitable routes and methods, for example, oral administration or parenteral (for example, intravenous) administration. The therapeutically effective amount of the compound of formula I or the pharmaceutically acceptable salt includes, but is not limited to, from about 0.0001 mg/kg weight/d to 20 mg/kg weight/d, for example, from 0.001 mg/kg weight/d to 10 mg/kg weight/d. The dosage and administration frequency of the compound of formula I depend on the requirements of a patient subject, for example, once daily or twice daily or more times daily. The administration can be intermittent. For example, a patient receives a daily dosage of the compound of formula I in a period of several days, and then the patient does not receive the daily dosage of the compound of formula I in the following several days or more days.

Anlotinib can be administered through various routes including, but not limited to, oral, parenteral, intraperitoneal, intravenous, intraarterial, transdermal, sublingual, intramuscular, rectal, transbuccal, intranasal, inhalation, vaginal, intraocular, topical, subcutaneous, intrafat, intraarticular, intraperitoneal and intrathecal administrations. In some specific embodiments, anlotinib is orally administered. The dosing amount of anlotinib can be determined according to the severity of the disease, the response of the disease, any treatment-associated toxicity, and the age and healthy condition of a patient. For example, the daily dosage of anlotinib can be 2 mg to 20 mg. In some embodiments, the daily dosage of the compound of formula I or the pharmaceutically acceptable salts thereof can be 2 mg, 3 mg, 4 mg, 5 mg, 6 mg, 7 mg, 8 mg, 9 mg, 10 mg, 11 mg, 12 mg, 13 mg, 14 mg, 15 mg and 16 mg. Anlotinib can be administered once daily or multiple times daily. In one embodiment, anlotinib is administered once daily in the form of an oral solid formulation.

The dosage regimen of anlotinib can be determined comprehensively depending on the activity and toxicity of the drug, tolerance of a patient, etc. Preferably, anlotinib is administered in an intermittent regimen. The intermittent regimen comprises a treatment period and a withdrawal period. In the treatment period, anlotinib can be administered once daily or multiple times daily. For example, a ratio of the treatment period to the withdrawal period in days is 2:0.5-2:5, preferably 2:0.5-2:3, more preferably 2:0.5-2:2, and most preferably 2:0.5-2:1. In some embodiments, anlotinib is administered continuously for 2 weeks and withdrawn for 2 weeks. In some embodiments, anlotinib is administered continuously for 2 weeks and withdrawn for 1 week. In some embodiments, anlotinib is administered continuously for 5 days and withdrawn for 2 days. For example, anlotinib can be orally administered once daily at a dosage of 6 mg, 8 mg, 10 mg or 12 mg for 2 weeks, and withdrawn for 1 week.

As used herein, the TLR7 agonist and anlotinib include non-salt forms thereof (for example, free acids or free bases), and also include pharmaceutically acceptable salts thereof. The non-salt forms and salt forms all fall within the protection scope of the present application. For example, the pharmaceutically acceptable salts of the TLR7 agonist can be hydrochloride, and the pharmaceutically acceptable salts of anlotinib can be hydrochloride or dihydrochloride.

The term "pharmaceutically acceptable" refers to a compound, material, composition and/or dosage form that is applicable to the contact with human and animal tissues without an excessive toxicity, irritation, allergic reaction or other problems or complications in the scope of reliable medical judgment, and is commensurate with an acceptable benefits/risk ratio.

The term "pharmaceutically acceptable salt" includes a salt formed from a basic radical and a free acid and a salt formed from an acidic radical and a free base, for example, hydrochloride, hydrobromide, nitrate, sulfate, phosphate, formate, acetate, trifluoroacetate, fumarate, oxalate, maleate, citrate, succinate, mesylate, benzenesulfonate and p-methylbenzenesulfonate, preferably, hydrochloride, hydrobromide, sulfate, formate, acetate, trifluoroacetate, fumarate, maleate, mesylate, p-methylbenzenesulfonate, sodium salt, potassium salt, ammonium salt and amino acid salt and so on. In the present application, when forming a pharmaceutically acceptable salt, a molar ratio of the free acid to the basic radical is about 1:0.5 to 1:5, preferably, 1:0.5, 1:1, 1:2, 1:3, 1:4, 1:5, 1:6, 1:7 or 1:8. In the present application, when forming a pharmaceutically acceptable salt, a molar ratio of the free base to the acidic radical is about 1:0.5 to 1:5, preferably, 1:0.5, 1:1, 1:2, 1:3, 1:4, 1:5, 1:6, 1:7 or 1:8.

As used herein, if a compound in the pharmaceutical combination of the present application has, for example, at least one basic site, an acid addition salt may be formed. If needed, a corresponding acid addition salt with an additional basic site may be further formed. A compound with at least one acidic group (for example, —COOH) can also form a salt with a base. A compound, for example, comprising both carboxyl and amino, can also form a corresponding inner salt.

The compounds of the present application may be asymmetric, for example, having one or more stereoisomers. Unless otherwise indicated, all stereoisomers, such as enantiomers and diastereomers, are included therein. The compounds containing asymmetric carbon atom(s) of the present application can be isolated in an optically active pure form or a racemic form. The optically active pure form can be resolved from a racemic mixture, or synthesized by using a chiral raw material or a chiral reagent.

The term "subject" is a mammal. In some embodiments, the subject is a mouse. In some embodiments, the subject is a human.

The term "about" shall be understood to include all values within a range of three standard deviations from a mean value or a standard tolerance range in a specific field. In some embodiments, the term "about" shall be understood as a variation not exceeding 0.5. The term "about" modifies all values listed thereafter. For example, "about 1, 2 and 3" represents "about 1", "about 2" and "about 3".

The term "pharmaceutical combination" refers to the simultaneous, parallel or sequential use of two or more active ingredients. The pharmaceutical combination allows the active ingredients to exhibit a cooperation (combination) effect. In some embodiments, the effect is a synergistic effect. The pharmaceutical combination includes a fixed combination or a non-fixed combination.

The term "fixed combination" refers to simultaneous administration of the active ingredients (for example, the TLR7 agonist or anlotinib) to a subject at a fixed total dosage or a fixed dosage proportion, or in the form of a single entity, pharmaceutical composition or formulation. In other words, the active ingredients are present in the same pharmaceutical formulation. In some embodiments, for example, the active ingredients are present in the same tablet, the same capsule, or the same sachet.

The term "non-fixed combination" refers to simultaneous, parallel, or sequential without specific time limitation administration of two or more active ingredients as independent entities (for example, a pharmaceutical composition and a pharmaceutical formulation) to a subject, wherein the active ingredients administered to the subject reach therapeutically effective amounts. An example of the non-fixed combination is a cocktail therapy. For example, three or more active ingredients are administered. In a non-fixed combination, each active ingredient can be packaged, sold or administered as a completely independent pharmaceutical composition. The "non-fixed combination" further includes the combined use of "fixed combinations", or a "fixed combination" and any one or more active ingredients as independent entities.

The term "pharmaceutical composition" refers to a mixture of one or more compounds or pharmaceutically acceptable salts thereof or the pharmaceutical combination or salt(s) thereof of the present application and a pharmaceutically acceptable excipient. The pharmaceutical composition is intended to facilitate the administration of the compounds or the pharmaceutical combination of the present application to a subject.

The term "synergistic effect" means that the effect (for example, inhibiting the growth of lung cancer cells or alleviating the symptoms of lung cancer) produced by a combination of two active ingredients (for example, the TLR7 agonist and anlotinib) is superior to the simple addition of the effect produced by the two active ingredients alone.

Administration Mode

The content below is not intended to limit the administration mode of the pharmaceutical combination of the present application.

The active ingredients in the pharmaceutical combination of the present application can be each formulated separately, or some or all of the active ingredients are co-formulated. In one embodiment, the pharmaceutical combination of the present application can be formulated into a pharmaceutical composition which is suitable for a single administration or multiple administrations.

The active ingredients in the pharmaceutical combination of the present application can be each administered separately, or some or all of the active ingredients are co-administered. The active ingredients in the pharmaceutical combination of the present application can be administered substantially at different times, or some or all of the active ingredients are administered substantially simultaneously.

The active ingredients in the pharmaceutical combination of the present application can be each administered independently in various suitable routes, or some or all of the active ingredients are co-administered in various suitable routes, including, but not limited to, oral administration or parenteral administration (intravenous, intramuscular, local or subcutaneous routes). In some embodiments, the active ingredients in the pharmaceutical combination of the present application can be each administered independently, or some or all of the active ingredients can be co-administered orally or by injection, for example, intravenous injection or intraperitoneal injection.

The active ingredients in the pharmaceutical combination of the present application can be each independent suitable dosage forms, or some or all of the active ingredients are co-formulated into a suitable dosage form, including, but not limited to, a tablet, lozenge, pill, capsule (for example, hard capsule, soft capsule, enteric capsule and microcapsule), elixir, granule, syrup, injection (intramuscular, intravenous or intraperitoneal injection), powder, emulsion, suspension, solution, dispersion and dosage forms of sustained-release preparations for oral or non-oral administration.

The active ingredients in the pharmaceutical combination of the present application can be each formulated independently with a pharmaceutically acceptable carrier and/or excipient, or some or all of the active ingredients are co-formulated with a pharmaceutically acceptable carrier and/or excipient.

The pharmaceutical combination may further comprise an additional therapeutic agent. In one embodiment, the additional therapeutic agent can be a known therapeutic agent for cancer in the art, preferably a therapeutic agent for lung cancer.

Technical Effects

The inventors of the present application have surprisingly found that the compound of formula I or the pharmaceutically acceptable salt thereof as the TLR7 agonist has good efficacy against lung cancer. Furthermore, the pharmaceutical combination of the TLR7 agonist and anlotinib also has good efficacy against lung cancer.

EXAMPLES

For clarity, the present invention is further described with the following examples, but the examples are not intended to limit the scope of the present application. All reagents are commercially available and can be used without further purification.

A method for preparing the compound of formula I of the present application and its in vitro binding activity to a Toll like receptor 7 can be seen in WO2016023511 and WO2017076346.

Example 1 Antitumor Experiment in LLC Mouse Model

In Example 1, the TLR7 agonist was

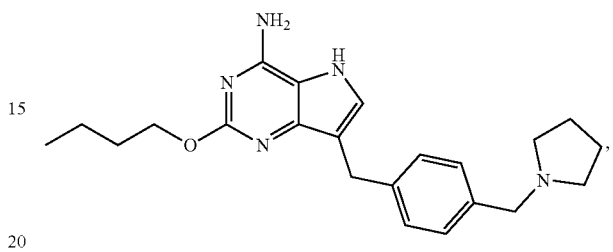

and anlotinib was anlotinib dihydrochloride.

LLC (Lewis Lung Cancer) Mice: subcutaneously grafted tumor cells of lung cancer (concentration: $2\times10^6$/mL$\times0.2$ mL/mouse) were inoculated into $C_{57}BL/6$ mice at the right side armpit (the site to be inoculated was shaved before inoculating) in a sterile environment, and passaged using a block insertion method. The C57BL/6 mice were female and 16-18 g in weight, and the breeding environment was SPF level. The diameter of the $C_{57}BL/6$ xenograft tumor was measured using a vernier caliper, and the animals were randomly divided into five groups when the tumors grew to 100-300 mm$^3$:
  i. Control group (blank control);
  ii. Monotherapy group: anlotinib 5 mg/kg/d (positive control), with normal saline as a vehicle;
  iii. Monotherapy group: TLR7 agonist 20 mg/kg, t.i.w., with ethanol/Tween 80 (v:v=1:1) as a vehicle;
  iv. Monotherapy group: anlotinib 1 mg/kg/d, with normal saline as a vehicle; and
  v. Combination therapy group: TLR7 agonist 20 mg/kg, t.i.w., and anlotinib 1 mg/kg/d.

The mice in the control group and monotherapy groups were administered in a volume of 10 mL/kg, and the mice in the combination therapy group were administered with two drugs simultaneously, each in a volume of 10 mL/kg. Weights and diameter of the tumor were measured every three days, and the behavior of mice was observed daily.

Mice were divided into groups on day 0, with 12 in the control group and 6 in each of the remaining groups. The drugs were administered intragastrically (i.g.) from day 1. The treatment was discontinued on day 12. During the experiment, the tumor volume was measured on days 0, 3, 6, 9, 12 and 15, and the tumors were removed and weighed on day 15, i.e., at the end of experiment.

The tumor volume and the tumor growth inhibition were calculated using the following formulae:

Tumor volume (TV)=($L\times W^2$)/2.

Tumor growth inhibition (TGI)=(1−tumor weight in the treatment group/tumor weight in the control group)×100%.

The results as shown in Table 1 indicated that the TLR7 agonist can inhibit the growth of LLC tumor, and its combined use with anlotinib can inhibit the growth of LLC tumor with a synergistic effect.

TABLE 1

Therapeutic Efficacy of TLR7 agonist and anlotinib against subcutaneous xenograft LLC tumor in mice

| Group | TV (mm³) on day 0 Mean ± SD | TV (mm³) on day 12 Mean ± SD | TV (mm³) on day 15 Mean ± SD | TGI (%) |
|---|---|---|---|---|
| Control group | 213.54 ± 38.13 | 2924.14 ± 885.32 | 4168.58 ± 1441.16 | — |
| Anlotinib 5 mg/kg/d × 11 d | 213.47 ± 38.16 | 1393.38 ± 532.59 | 1811.75 ± 736.45 | 63.4% |
| TLR7 agonist 20 mg/kg, t.i.w. | 212.98 ± 47.17 | 2353.68 ± 663.83 | 3257.62 ± 577.45 | 30.1% |
| Anlotinib 1 mg/kg/d × 11 d | 213.25 ± 39.34 | 2697.21 ± 747.99 | 4114.08 ± 1213.40 | 13.5% |
| TLR7 agonist 20 mg/kg, t.i.w. + anlotinib 1 mg/kg/d × 11 d | 213.71 ± 50.55 | 1244.28 ± 230.68 | 1635.23 ± 367.45 | 65.4% |

The invention claimed is:

1. A pharmaceutical combination, comprising a TLR7 agonist or a pharmaceutically acceptable salt thereof, and anlotinib or a pharmaceutically acceptable salt thereof, wherein the TLR7 agonist is 2-butoxy-7-(4-(pyrrolidin-1-ylmethyl)benzyl)-5H-pyrrolo[3,2-d]pyrimidin-4-amine

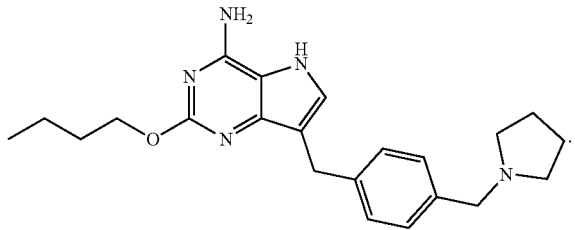 [SMILES: CCCCOc1nc(N)c2[nH]cc(Cc3ccc(CN4CCCC4)cc3)c2n1]

2. The pharmaceutical combination according to claim 1, wherein the pharmaceutical combination is selected from a fixed combination or a non-fixed combination.

3. A method for treating lung cancer, comprising administering to a subject in need thereof an effective amount of the pharmaceutical combination according to claim 1.

4. The method according to claim 3, wherein the lung cancer is small cell lung cancer.

5. The method according to claim 3, wherein the lung cancer is non-small cell lung cancer.

6. The pharmaceutical combination according to claim 2, wherein the fixed combination is in the form of a solid pharmaceutical composition.

7. The pharmaceutical combination according to claim 2, wherein the TLR7 agonist and alotinib or a pharmaceutically acceptable salt thereof in the non-fixed combination are each in the form of a solid pharmaceutical composition.

8. The pharmaceutical combination according to claim 6, wherein the solid pharmaceutical composition is selected from the group consisting of a tablet and a capsule.

9. The pharmaceutical combination according to claim 7, wherein the solid pharmaceutical composition is selected from the group consisting of a tablet and a capsule.

10. The pharmaceutical combination according to claim 1, wherein the pharmaceutical combination comprises 0.0001 mg/kg/d to 20 mg/kg/d of 2-butoxy-7-(4-(pyrrolidin-1-ylmethyl) benzyl)-5H-pyrrolo[3,2-d]pyrimidin-4-amine or a pharmaceutically acceptable salt thereof, and 1 mg/kg/d of anlotinib dihydrochloride.

11. The pharmaceutical combination according to claim 1, wherein the pharmaceutical combination comprises 0.0001 mg/kg/d to 10 mg/kg/d of 2-butoxy-7-(4-(pyrrolidin-1-ylmethyl) benzyl)-5H-pyrrolo[3,2-d]pyrimidin-4-amine or a pharmaceutically acceptable salt thereof, and 1 mg/kg/d of anlotinib dihydrochloride.

12. The pharmaceutical combination according to claim 1, wherein the pharmaceutical combination comprises 0.0001 mg/kg/d to 20 mg/kg/d of 2-butoxy-7-(4-(pyrrolidin-1-ylmethyl) benzyl)-5H-pyrrolo[3,2-d]pyrimidin-4-amine or a pharmaceutically acceptable salt thereof, and anlotinib dihydrochloride at a dosage of 6 mg, 8 mg, 10 mg or 12 mg once daily.

13. The pharmaceutical combination according to claim 1, wherein the pharmaceutical combination comprises 0.001 mg/kg/d to 10 mg/kg/d of 2-butoxy-7-(4-(pyrrolidin-1-ylmethyl) benzyl)-5H-pyrrolo[3,2-d]pyrimidin-4-amine or a pharmaceutically acceptable salt thereof, and anlotinib dihydrochloride at a dosage of 6 mg, 8 mg, 10 mg or 12 mg once daily.

14. The pharmaceutical combination according to claim 1, wherein the pharmaceutical combination comprises 0.0001 mg/kg/dose to 20 mg/kg/dose of 2-butoxy-7-(4-(pyrrolidin-1-ylmethyl)benzyl)-5H-pyrrolo[3,2-d]pyrimidin-4-amine or a pharmaceutically acceptable salt thereof administered thrice weekly, and 1 mg/kg/d of anlotinib dihydrochloride administered for 11 days continuously.

15. The pharmaceutical combination according to claim 1, wherein the pharmaceutical combination comprises 0.001 mg/kg/dose to 10 mg/kg/dose of 2-butoxy-7-(4-(pyrrolidin-1-ylmethyl)benzyl)-5H-pyrrolo[3,2-d]pyrimidin-4-amine or a pharmaceutically acceptable salt thereof administered thrice weekly, and 1 mg/kg/d of anlotinib dihydrochloride administered for 11 days continuously.

* * * * *